United States Patent
Cassin et al.

(10) Patent No.: US 11,077,037 B2
(45) Date of Patent: Aug. 3, 2021

(54) STABLE COSMETIC COMPOSITION CONTAINING A MONOGLYCERIDE, A TARTARIC ESTER OF MONOGLYCERIDE, AND A COATED FILLER

(71) Applicant: L'OREAL, Paris (FR)

(72) Inventors: Guillaume Cassin, Villebon sur Yvette (FR); Sylvie Poret Fristot, Rungis (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/359,404

(22) Filed: Mar. 20, 2019

(65) Prior Publication Data
US 2019/0216701 A1  Jul. 18, 2019

Related U.S. Application Data

(62) Division of application No. 14/900,787, filed as application No. PCT/EP2014/063445 on Jun. 25, 2014, now abandoned.

(30) Foreign Application Priority Data

Jun. 28, 2013 (FR) ..................... 1356283

(51) Int. Cl.
| | |
|---|---|
| *A61Q 19/00* | (2006.01) |
| *A61K 8/37* | (2006.01) |
| *A61K 8/29* | (2006.01) |
| *A61K 8/891* | (2006.01) |
| *A61K 8/02* | (2006.01) |
| *A61K 8/04* | (2006.01) |

(52) U.S. Cl.
CPC ............ *A61K 8/375* (2013.01); *A61K 8/0241* (2013.01); *A61K 8/042* (2013.01); *A61K 8/29* (2013.01); *A61K 8/891* (2013.01); *A61Q 19/008* (2013.01); *A61K 2800/43* (2013.01); *A61K 2800/591* (2013.01); *A61K 2800/622* (2013.01); *A61K 2800/624* (2013.01)

(58) Field of Classification Search
CPC .......... A61K 8/42; A61K 8/29; A61K 8/0241; A61K 8/375; A61K 8/891; A61K 2800/43; A61K 2800/591; A61Q 19/008
See application file for complete search history.

(56) References Cited

U.S. PATENT DOCUMENTS

| | | | |
|---|---|---|---|
| 4,877,604 A | 10/1989 | Schlossman | |
| 5,707,437 A * | 1/1998 | Niedenzu | C09C 3/12 106/446 |
| 5,770,185 A * | 6/1998 | Wachter | A61K 8/37 424/400 |
| 6,667,044 B1 * | 12/2003 | Diec | A61K 8/042 424/401 |
| 2004/0086470 A1 | 5/2004 | Nieendick et al. | |
| 2007/0154500 A1 | 7/2007 | Cassin et al. | |
| 2008/0050398 A1 | 2/2008 | Bockmuehl et al. | |

FOREIGN PATENT DOCUMENTS

| | | |
|---|---|---|
| CN | 101366403 A | 2/2009 |
| CN | 101731298 A | 6/2010 |
| CN | 102845540 A | 1/2013 |
| WO | WO-01/24643 A1 | 4/2001 |
| WO | WO-01/54512 A1 | 8/2001 |
| WO | WO-2008/050398 A1 | 5/2008 |

OTHER PUBLICATIONS

Unknown author, title: May vs. Might: What's the Difference? online publication by writing explained. Downloaded from https://writingexplained.org on Feb. 12, 2020 (Year: 2020).*
Talaat et al, title: Lecithin microemulsion lipogels versus conventional gels for skin Targeting of Terconazole: In Vitro, Ex Vivo, and In Vivo Investigation; AAPS PharmSciTech, vol. 20, issue 161, published inline Apr. 10, 2019. (Year: 2019).*
Danisco, title: PANODAN® A2020 Kosher; product description, May 2012. (Year: 2012).*
Abstract of CN-101366403-A—XP002722763.
Abstract of CN-101731298-A—XP002722765.
Abstract of CN-102845540-A—XP002722764.
International Search Authority; Written Opinion of the International Search Authority for corresponding PCT/EP2014/063445.

* cited by examiner

*Primary Examiner* — Yanzhi Zhang
(74) *Attorney, Agent, or Firm* — Polsinelli PC

(57) ABSTRACT

Provided is a composition, especially a cosmetic composition, that comprises at least one monoglyceride and at least one tartaric ester of monoglyceride, and at least one coated pigment and/or mineral filler. Also provided is the use of a coated pigment and/or coated mineral filler for improving the stability of a composition, especially a cosmetic composition comprising at least one monoglyceride and at least one diacetyl tartaric ester of monoglyceride. Further provided is a cosmetic treatment method that implements the composition of the invention.

11 Claims, No Drawings

STABLE COSMETIC COMPOSITION CONTAINING A MONOGLYCERIDE, A TARTARIC ESTER OF MONOGLYCERIDE, AND A COATED FILLER

CROSS REFERENCE TO RELATED APPLICATIONS

This application is a Divisional of application Ser. No. 14/900,787 filed on Jun. 25, 2014, which is a National Phase filing under 35 U.S.C. § 371 of PCT/EP2014/063445 filed on Jun. 25, 2014; and this application claims priority to Application No. 1356283 filed in France on Jun. 28, 2013. The entire contents of each application are hereby incorporated by reference.

The invention relates to a stable cosmetic composition specially adapted to limit or reduce the brightness or shiny appearance of the skin, especially in tropical climate conditions.

The shiny appearance that the skin has in conditions of substantial temperature and relative humidity characteristic of tropical areas, is related to a flow of sebum and sweat during the day. This phenomenon of shine of the skin thus affects both populations that are or are not "oily skin". It also results in a sticky and dirty feeling of the skin during the day which is particularly resented by people living in these areas of the world.

To date, the use of particles of mineral or organic fillers to matt the skin is known to those skilled in the art. Unfortunately, these particles have the effect of acting on the sebum but not on sweating. Compositions containing such mineral or organic fillers do not make it possible to sustainably reduce skin shine in extreme conditions (substantial temperature and relative humidity). The use of aluminum salts to reduce sweating is also known but for obvious reasons of comfort their use on the face is not possible.

There is therefore a need for cosmetic compositions, preferably comfortable and moisturizing, that sustainable reduce the brightness of skin in substantial temperature and relative humidity conditions.

The invention has for purpose to provide compositions, in particular cosmetic compositions, that make it possible to reduce, preferably sustainably, the gloss or shiny appearance of skin exposed to a tropical climate.

The invention particularly has for purpose to provide an aqueous cosmetic composition that is stable over time to solve the problems mentioned hereinabove.

Moreover, the invention also has for purpose to provide a pleasant cosmetic and/or comfortable for the user, particularly when being felt for application to the skin.

The invention also has for purpose to provide a composition, in particular a cosmetic composition, that has moisturizing properties.

The invention has for purpose to overcome all these technical problems in an industrial, reliable, and repeatable manner, and at low cost.

Surprisingly, the inventors discovered that it was possible to achieve the aforementioned objectives thanks to a composition, in particular cosmetic, comprising at least one monoglyceride and at least one tartaric ester of monoglyceride and at least one coated pigment and/or at least one coated mineral filler.

The invention further relates to the use of a combination of at least one monoglyceride and at least one monoglyceride diacetyl tartaric ester to limit the sheen or gloss of the skin, especially in a tropical climate.

In terms of the invention, the term "tropical climate" means especially a climate in an area of the globe between the tropics, generally up to about 15° or 20° north and south latitude. This is a non-arid climate where the monthly average temperature does not fall below 18° C. all throughout the year. Tropical climates have a dry season and a wet season. In general, tropical climates have an annual rainfall generally between 1 and 2 m. The invention in particular covers compositions, including cosmetics, adapted to the climate of China, India, Brazil, and countries with equivalent climate conditions.

A tropical climate thus includes substantial temperature and relative humidity likely to generate a significant flow of sebum and sweat during the day, even for skins that are outside of these not particularly oily climates. This phenomenon of gloss or shine of the skin thus affects both populations that are or are not "oily skin".

However the compositions of the invention are not limited to use in a tropical climate and can be used in any climate, particularly for the purposes of limiting the glossy or shiny appearance of the skin.

Advantageously, the composition comprises an aqueous phase. A composition according to the invention may comprise more than 50%, and preferably between 60% and 95%, and more preferably between 65% and 95% by mass of aqueous phase with respect to the total mass of the composition.

Preferably, the composition according to the invention contains a lipogel phase.

Aqueous systems based on the combination of monoglyceride and a tartaric ester of monoglycerides, are commonly known as lipogels and have been used in food for a few years now to make lighter margarines. A lipogel generally comprises a three-dimensional matrix containing a non-aqueous continuous phase. A lipogel is a complex system that is generally comprised of percolated fatty body crystals in an aqueous phase. The size of such crystals is generally a few tens of micrometers. A lipogel is generally formed by cooling a hot-forming composition (here, a temperature above 55° C.) a lamellar phase visible under optical microscope in bi-refracting light. Such a three-dimensional architecture can contain up to 98% of an aqueous phase.

These systems have undergone significant structural studies. Mention may be made of the following articles, among others.

Liquid Crystalline Phases in the Structuring of Food Products, 1998, Lebensmittel-Wissenschaft und-technologie, 31, 387-396, Investigation of the Gel to Coagel Phase Transition in Monoglyceride-Water Systems (Langmuir 1998, 14, 5757-5763)

Lipid organization and dynamics of the monostearoylglycerol-water system. A 2H NMR study (Chemistry and Physics of lipids 109 (2001) 15-28)

Rheological Characterization, Crystallization, and Gelation (Behavior of Monoglyceride Gels (Journal of Colloid and Interface Science 249, (2002) 412-422).

The use of monoglyceride stearate in cosmetics for stabilizing emulsions has long been known and can be considered to be in the public domain. However, the use of a tartaric ester of monoglyceride is less common.

The compositions according to the invention are preferably in the form of creams, foams or sticks. It is important to note that the compositions according to the invention, if they have the appearance of cosmetic creams have, when observed under a microscope, a structure different from conventional emulsions characterized for example by a regular carpet of droplets. The compositions according to the invention are characterized in particular by a highly birefringent appearance in polarized light which is typical of their semi-crystalline nature.

The percentages of the constituents are given in mass relative to the total mass of the composition, unless mentioned otherwise.

Monoglyceride

A monoglyceride, or monoacylglycerol (MAG), is a glyceride forms from a fatty acid residue combined with a glycerol residue by an ester bond. They can be classified into two groups, 1-monoacylglycerols and 2-monoacylglycerols according to whether the acyl group is in position 1 or 2 of the glycerol residue.

According to a particular embodiment, the composition comprises as a monoglyceride one or more monoglycerides comprising an alkyl chain, saturated or unsaturated, comprising from 12 to 22 carbon atoms.

Preferably the monoglyceride comprises an alkyl chain, saturated or unsaturated, comprising 16 or 18 carbon atoms.

In this case, interested is particularly given to 1-monoacylglycerols, such as those of the following formula (e.g. C18):

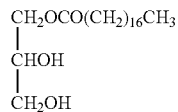

The length of the fatty acid chain can range from C12 to C22, preferably esters of C16 or C18 monoglycerides are chosen.

The raw material used is important in that the monoglycerides used allow a lipogel phase to be formed. Monoglycerides containing less than 10% residual diglycerides are in particular used. Monoglyceride stearates are preferably used, for example marketed under the name HP DIMODAN by DANISCO company or those sold under the name TEGIN 90 by the company EVONIK GOLDSCHMIDT.

The monoglyceride content of the formulations according to the invention is from 1% to 20%, preferably from 2 to 10% and very preferably from 3 to 8% by mass based on the total mass of said composition.

Tartaric Ester of Monoglycerides of Fatty Acids

Tartaric esters of monoglycerides of fatty acids are usually obtained by grafting a tartaric residue at position 3 of the glycerol residue of a 1-monoacylglycerol. The length of the fatty acid chain can range from C12 to C22, preferably esters of C16 or C18 monoglycerides will be chosen.

The tartaric ester of monoglyceride is preferably a diacetyl tartaric ester of monoglyceride comprising an alkyl chain, saturated or unsaturated, comprising from 12 to 22 carbon atoms, and preferably comprising 16 or 18 carbon atoms.

In this case, particular interest is given to diacetyl tartaric acid esters of C18 monoglycerides, such as those of the following formula:

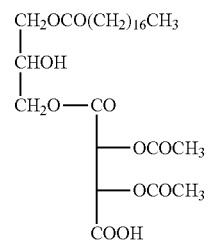

The invention covers the various isomers of tartaric acid and mixtures thereof, including racemic mixtures.

These ingredients and their uses are described on pages 88-95 of the Functional Ingredients for Food brochure published by DANISCO and available on the http://www.danisco.com/site.

These esters can be chosen among tartaric ester of mono- and diglycerides of fatty acids (E472d additive), and a monoacetyltartric ester of mono- and diglycerides of fatty acids (E472e additive). Monoglycerides and diglycerides esters with a purity of about 80% or more are mainly sought.

The tartaric ester of monoglycerides content of the formulations according to the invention is from 0.05% to 5%, preferably from 0.1 to 2% and very preferably from 0.1 to 1% by mass based on the total mass of said composition. Typically a tartaric ester monoglyceride is used with a content of 0.2-0.5% by mass based on the total mass of said composition.

Mineral Fillers and Coated Pigments

Pigments and/or mineral fillers used in the invention are surface treated, entirely or partially, by at least one hydrophobic treatment agent.

The surface treatment of a pigment and/or mineral filler according to the invention generally denotes the full or partial surface treatment of the pigment by a surface agent, absorbed, adsorbed or grafted onto said pigment and/or mineral filler. The surface-treated pigments and/or mineral filler may be prepared using chemical, electronic, mechanochemical or mechanical surface treatment techniques well known to those skilled in the art. Commercial products may also be used. The surface agent may be absorbed, adsorbed or grafted onto the pigments and/or mineral filler by means of solvent evaporation, chemical reaction and/or creation of a covalent bond.

"Pigment" denotes a solid particle, white or colored, naturally insoluble in the liquid hydrophilic and lipophilic phases usually used in cosmetics or insolubilized by formulation in the form of lacquer, where applicable. As pigments, mention can be made of organic and inorganic pigments such as those defined and described in Ullmann's Encyclopedia of Industrial Chemistry "Pigment organics", 2005 Wiley-VCH Verlag GmbH & Co. KGaA, Weinheim, et "Pigments, Inorganic, 1. General" 2009 Wiley-VCH Verlag GmbH & Co. KGaA, Weinheiml.

The mineral fillers according to the invention are inorganic pigments.

Examples include azoic pigments that contain one or more azoic groups A-N=N-B with A representing a (hetero) aryl optionally substituted, B representing (hetero)aryl optionally substituted or —CH[C(0)-R]—C(0)-X,-A', A' representing a (hetero)aryl, optionally substituted, and R representing a hydrogen atom or a (C,-C6)alkyl, with the groups A, A' and B (hetero)aryl which contain no solubilizing groups such as —SO3H, —COOH. They can be especially monoazoic for which the 3-Naphthols, monoazopyrrolone pigments, Benzimidazolone pigments; diazoic pigments such as diazodiarylide pigments and Bis (N-acetoacetarylide), the trisazoic or tetraazoic pigments. Mention can also be made of Azoic Pigments with Metal Complexes or "azo metal complex pigment".

Other pigments are also of interest, these are isoindolinone and isoindoline pigments, Phthalocyanine pigments; Quinacridone pigments; the Perinone pigments; Perylene pigments; Anthraquinone pigments such as Hydroxyanthraquinone Pigments; Aminoanthraquinone the pigments including Acylaminoanthraquinones and Anthraquinone Azoic pigments; Heterocyclic Anthraquinones; Anthraquinone polycarbocyclic pigments; Pyranthrone pigments; Anthanthrone pigments; Diketopyrrolopyrrole pigments (DPP); Thioindigo pigments; Dioxazines pigments; Triphenylmethane pigments; Quinophthalone pigments; and Fluorescent pigments.

In the context of this invention, the pigment may be at least partially organic. According to one embodiment of the invention, the pigment is an organic pigment. According to another embodiment of the invention, the pigment is an mineral pigment.

As illustrations of pigments that can be used in this invention, mention can be made of carbon black, titanium oxide, chromium oxide, pigments of the type D&C, FD&C and lacquers thereof, and in particular those under the names D&C Blue no. 4, D&C Brown no. 1, FD&C Green no. 3, D&C Green no. 5, D&C Green no. 6, FD&C Green no. 8, 20 D&C Orange no. 4, D&C Orange no. 5, D&C Orange no. 10, D&C Orange no. 11, FD&C Red no. 4, D&C Red no. 6, D&C Red no. 7, D&C Red no. 17, D&C Red no. 21, D&C Red no. 22, D&C Red no. 27, D&C Red no. 28, D&C Red no. 30, D&C Red no. 31, D&C Red no. 33, D&C Red no. 34, D&C Red no. 36, FD&C Red no. 40, FD&C Red 40 lake, D&C Violet no. 2, Ext. D&C Violet no. 2, FD & C Blue no. 1, D&C Yellow no. 6, FD&C Yellow no. 6, D&C Yellow no. 7, 25 Ext. D&C Yellow no. 7, D&C Yellow no. 8, D&C Yellow no. 10 or D&C Yellow no. 11, with the understanding that when said pigment is not naturally insoluble in the hydrophilic and lipophilic phases usually used in cosmetics, it is used in the form of a corresponding lacquer. As examples of lacquers, mention may be made lacquers based on barium, strontium, calcium, aluminum, or diketo pyrrolopyrroles. Other examples of pigments that can be used in this invention, mention can be made in particular of surface treated and/or coated mineral pigments, and in particular titanium dioxide, zirconium oxide or cerium oxide, as well as zinc oxide, iron oxide (black, yellow or red) or chromium oxide, manganese violet, ultramarine blue, chromium hydrate and ferric blue, or metal powders such as aluminum powder, copper powder, gold powder and silver powder. Mention may also be made of optical effect pigments such as particles comprising a natural or synthetic organic or inorganic substrate, for example glass, acrylic resins, polyester, polyurethane, polyethylene terephthalate, ceramics or aluminas, said substrate and being coated or not with metallic substances such as aluminum, gold, silver, platinum, copper, bronze, or with metal oxides such as titanium dioxide, iron oxide, chromium oxide. This can also be nacres. The term "nacres" should be understood to denote iridescent pigments, in particular produced by some mollusks in their shell or by synthetic means. The pearlescent pigments may be chosen from mica coated with titanium, or bismuth oxychloride, titanium mica coated with iron oxides, titanium mica coated with iron blue and chromium oxide in particular, titanium mica coated with an organic pigments of the aforementioned type and pearlescent pigments based on bismuth oxychloride. Interference pigments may also be used, in particular liquid crystal or multilayer pigments. The pigments may also be pigments having a structure that may be, for example, of sericite/brown iron oxide/titanium dioxide/silica type. These can also be pigments having a structure that may, for example, be of the type of silica microspheres containing iron oxide.

Examples of pigments particularly suitable for the implementation of this invention, mention may be made of D&C Red no. 7, titanium oxide, chromium oxide, lacquer-type pigments of D&C and FD&C cited above, and in particular D&C Red No. 22 Lake, Yellow no. 6 lake, FD&C Blue no. 1 lake. The pigments in accordance with the invention can have the form of powder or pigment paste. The pigments in accordance with the invention can for example be chosen from white or colored pigments, lakes, pigments with special effects such as nacres or flakes, and mixtures thereof. Examples of white or colored inorganic pigments include oxides of zirconium or of cerium, chromium oxides, manganese violet, ultramarine blue, chromium hydrate, and ferric blue. Examples of white or colored organic pigments include the compounds nitroso, nitro, azo, xanthene, quinoline, anthraquinone, phthalocyanine, metal complex type, isoindolinone, isoindoline, quinacridone, perinone, perylene, diketopyrrolopyrrole, thioindigo, dioxazine, triphenylmethane quinophthalone.

In particular, white or colored organic pigments can be chosen from carmine, carbon black, aniline black, azo yellow, quinacridone, phthalocyanine blue, sorghum red, the blue pigments codified in the Color Index under the references CI 42090, 69800, 69825, 73000, 74100, 74160, the yellow pigments codified in the Color Index under the references CI 11680, 11710, 15985, 19140, 20040, 21100, 21108, 47000, 47005 the green pigments codified in the Color Index under the references CI 61565, 61570, 74260, the orange pigments codified the Color Index under the references CI 11725, 15510, 45370, 71105, the red pigments codified in the Color Index under CI 12085 references, 12120, 12370, 12420, 12490, 14700, 15525, 15580, 15620, 15630, 15800, 15850, 15865, 15880, 17200, 26100, 45380, 45410, 58000, 73360, 73915, 75470, and the pigments obtained by oxidative polymerization of indole or phenolic derivatives as described in patent FR 2 679 771.

Pigment pastes of organic pigment can be used such as products sold by the company HOECHST under the name: —JAUNE COSMENYL 10G: Pigment YELLOW 3 (CI 11710); —JAUNE COSMENYL G: Pigment YELLOW 1 (CI 11680); —ORANGE COSMENYL GR: Pigment ORANGE 43 (CI 71105); —ROUGE COSMENYL R: Pigment RED 4 (CI 12085); —CARMIN COSMENYL FB: Pigment RED 5 (CI 12490); —VIOLET COSMENYL RL: Pigment VIOLET 23 (CI 51319); —BLEU COSMENYL A2R: Pigment BLUE 15.1 (CI 74160); —VERT COSMENYL GG: Pigment GREEN 7 (CI 74260); —NOIR COSMENYL R: Pigment BLACK 7 (CI 77266). The pigments in accordance with the invention can also be in the form of composite pigments such as described in patent EP 1 184 426. These composite pigments may be composed of particles comprising: —a mineral core, —at least one binder for fixing the organic pigments to the core, and—at least one organic pigment at least partially covering the core. The term lacquer means dyes adsorbed on insoluble particles, the assembly thus obtained remaining insoluble during use. The inorganic substrates onto which the dyes are adsorbed are for example alumina, silica, borosilicate, calcium and sodium or calcium aluminum borosilicate, and aluminum. Among the organic dyes, mention can be made of cochineal carmine. Examples lacquers include products known under the following names: D & C Red 21 (CI 45 380), D & C Orange 5 (CI 45 370), D & C Red 27 (CI 45 410), D & C Orange 10 (CI 45 425), D & C Red 3 (0145 430), D & C Red 7 (0115 850:1), D & C Red 4 (0115 510), D & C Red 33 17 200), D & C Yellow 5 (CI 19 140), D & C Yellow 6 (CI 15 985), D & C Green (CI 61 570), D & C Yellow 10 (CI 77 002), D & C Green 3 (CI 42 053), D & C Blue 1 (CI 42 090). The term special effect pigments means pigments that generally create a colored appearance (characterized by a certain shade, a certain vivacity and a certain lightness) non-uniform and changeable according to the viewing conditions (light, temperature, viewing angles, etc.). They are opposed by the same token with white or colored pigments, which provide a conventional uniform opaque, semitransparent or transparent.

Examples of special effect pigments include white pearlescent pigments such as mica coated with titanium or with bismuth oxychloride, colored pearlescent pigments such as mica coated with titanium and iron oxides, mica coated with titanium and especially ferric or blue and chromium oxide, mica coated with titanium and with an organic pigment as defined above, and nacreous pigments based on bismuth oxychloride. Also, exemplary pigments loose interference effect on a substrate such as liquid crystals (Helicones HC from Wacker), holographic interference flakes (Geometric Pigments or Spectra f/x from Spectratek). Pigments with special effects also comprise fluorescent pigments, whether substances which are fluorescent in daylight or which produce ultraviolet fluorescence, phosphorescent pigments, photochromic pigments, thermochromic pigments and quantum dots, for example sold by Quantum Dots Corporation. Quantum dots are light conductive semiconductor nanoparticles capable of emitting, under light excitation, radiation having a wavelength between 400 nm and 700 nm. These nanoparticles are known from literature. In particular, they can be manufactured by the methods described for example in U.S. Pat. Nos. 6,225,198 and 5,990,479, in the publications cited therein, and in the following publications as well: Dabboussi B. O. et al "(CdSe)ZnS core-shell quantum dots: synthesis and characterisation of a size series of highly luminescent nanocristallites" Journal of physical chemistry B, vol 101, 1997, pp 9463-9475. et Peng, Xiaogang et al, "Epitaxial Growth of highly Luminescent CdSe/CdS core/shell nanocrystals with photostability and electronic accessibility" Journal of the American Chemical Society, vol 119, no. 30, pp 7019-7029.

The pigments according to the invention are preferably colored pigments.

The variety of pigments involved provides a rich palette of colors as well as specific optical effects, such as metallic effects, interference. The size of a pigment other than the nacres in solution is generally between 10 nm and 10 pm, preferably between 50 nm and 5 pm, and even more preferably between 100 nm and 3 pm. The size of a nacre in solution is generally between 1 and 200 pm, preferably between 1 nm and 80 pm, and even more preferably between 1 and 50 pm. Among the inorganic pigments, mention can be made for example of titanium dioxide (rutile or anatase) optionally surface treated and codified in the Color Index under the reference C177891; black iron oxides, red and yellow brown, codified under references C177499, 77492, 77491; manganese violet (C177742); ultramarine blue (C177007); hydrated chromium oxide (C177289); ferric blue (C177510).

Among the organic pigments that may be mentioned, for example, the particular pigment YELLOW 3 sold under the trade name "JAUNE COVANOR W 1603 by WACKHERR (CI 17710), "D & C RED no. 19" (CI 45170), D & C RED no. 9 (CI 15585), D & C RED no. 21 (CI 45380), D & C ORANGE no. 4 (CI 15510), D & C ORANGE no. 5 (CI 45370), D & C RED no. 27 (C145410), D & C RED no. 13 (CI 15630), D & C RED no. 7 (CI 15850-1), D & C RED no. 6 (CI 15850-2), D & C YELLOW no. 5 (CI 19140), D & C RED no. 36 (CI 12085), D & C ORANGE no. 10 (CI 45425), D & C YELLOW no. 6 (CI 15985), D & C RED no. 30 (CI 73360), D & C RED no. 3 (CI 45430), carbon black (CI 77266), and lakes based on cochineal carmine (CI 75470).

Pearlescent pigments can also be used, and in particular chosen from white pearlescent pigments such as mica coated with titanium oxide, bismuth oxide; colored pearlescent pigments such as titanium mica with iron oxides, titanium mica with ferric blue or chromium oxide, titanium mica with an organic pigment of precipitated type, as well as those based oxychloride bismuth.

The content of pigments and/or coated mineral fillers may advantageously range from 0.1% to 4% by mass, preferably from 0.2% to 3% by mass based on the total mass of said composition.

Hydrophobic Treatment Agent (or Lipophilic)

According to a particular embodiment of the invention, the pigments and/or mineral fillers may be surface treated or coated with at least one hydrophobic or lipophilic-treating agent selected from silicone surfactants; fluorinated surfactants; surfactants fluorosilicone; metal soaps, amino N-acylamino acids or salts thereof such as disodium stearoyl glutamate; lecithin and its derivatives; triisostearyl isopropyl titanate; isostearyl sebacate; plant or animal natural waxes, synthetic waxes polar; fatty esters; fatty alcohols; phospholipids, and mixtures thereof. As surfactants, mention may be made of silicone polydimethylsiloxanes.

The treatment agent may represent from 0.1 50% by mass, and particularly from 0.5 to 5 mass %, of the total mass of the coated pigment and the coated mineral filler.

Sequestrant

In an alternative embodiment of the invention, formulas can furthermore contain one or more sequestering agents.

Sequestering agents are molecules which form chemical complexes with metallic ions such as copper, iron and nickel.

Generally, sequestering agents or chelating agents are described in KIRK-OTHMER Encyclopedia of Chemical Technology Encyclopedia John Wiley and Sons Vol 5 pages 708-739.

Among the sequestering agents that can be used in the composition of the invention, mention can be made of for example ethylene diamine tetraacetic acid (EDTA) and its salts such as disodium salt of ethylene diamine tetraacetic acid (disodium EDTA); the phosphonic derivatives such as hexamethylene diamine tetra (methylene phosphonic acid), ethylenediamine acid tetra (methylenephosphonic) acid, 1-hydroxyethylidene 1,1-diphosphonic acid, amino tri (methylene phosphonic acid), the acid diethylene triamine penta (methylene phosphonic acid), and salts and especially sodium salts thereof such as the pentasodium salt of ethylenediamine tetra (methylene phosphonic acid); the particular polyamine polymers such as polyalkylene polyamines and derivatives thereof, and in particular polyethyleneimine, and dendrimers containing chelating activity; proteins, such as spermine, spermidine, transferrin, ferritin; carboxylic acids such as phytic acid, citric acid, malic acid, nitrilo acetic acid, fumaric acid, tartaric acid, succinic acid, oxalic acid, mucic acid; methylglycine diacetic acid, N-lauroyl-N, N',N'-tri-acetic ethylenediamine, iminodisuccinic acid, acid N,N-dicarboxymethyl L-glutamic ethylenediamine-N,N'-dissucinique, desferrioxamine mesylate; glucono delta-lactone, sodium gluconate, potassium and/or calcium; phosphoric acid, potassium bitartrate, sodium acetate, sorbitol and mixtures of these sequestering agents.

The preferred sequestering agents are ethylene diamine tetraacetic acid (EDTA), glucono delta-lactone, sodium gluconate, potassium and/or calcium; citric acid, phosphoric acid, tartaric acid, potassium bitartrate, sodium acetate, sorbitol.

Preferably, EDTA is used.

Preferably, the sequestrant content levels are from 0.01% to 1%, and preferably from 0.05 to 0.5%, by mass based on the total mass of said composition.

The invention particularly relates to a composition, especially a cosmetic composition, comprising as an ingredient of the composition (i) at least one or more monoglycerides comprising an alkyl chain, saturated or unsaturated, comprising from 12 to 22 carbon atoms, and preferably comprising 16 or 18 carbon atoms, (ii) at least one of monoglyceride diacetyl tartaric ester comprising an alkyl chain, saturated or unsaturated, comprising from 12 to 22 carbon atoms, and preferably comprising 16 or 18 carbon atoms (iii) at least one pigment and/or coated mineral filler, and (iv) optionally at least one sequestering agent.

Advantageously, the composition of the invention is a composition, especially a cosmetic composition, comprising as an ingredient of the composition (i) at least one or more monoglycerides comprising an alkyl chain, saturated or unsaturated, comprising from 12 to 22 carbon atoms (ii) at least a diacetyl tartaric ester of monoglyceride comprising an alkyl chain, saturated or unsaturated, comprising from 12 to 22 carbon atoms, and preferably comprising 16 or 18 carbon atoms, (iii) at least one pigment and/or coated mineral filler, and (iv) optionally at least one of the sequestering agents or any combinations thereof: ethylene diamine tetraacetic acid (EDTA), glucono delta-lactone, sodium gluconate, potassium and/or calcium; citric acid, phosphoric acid, tartaric acid, potassium bitartrate, sodium acetate, sorbitol, and preferably EDTA.

Advantageously, the composition of the invention is a composition, especially a cosmetic composition, comprising among the composition ingredients (i) at least one or more monoglycerides comprising an alkyl chain, saturated or unsaturated, comprising 16 or 18 C atoms, (ii) at least one of monoglyceride diacetyl tartaric ester comprising an alkyl chain, saturated or unsaturated, comprising 16 or 18 carbon atoms, (iii) at least one pigment and/or coated mineral filler, and (iv) optionally at least one sequestering agent at least one sequestering agent, preferably selected from the following agents or any combination thereof: ethylene diamine tetraacetic acid (EDTA), glucono delta-lactone, sodium gluconate, potassium and/or calcium; citric acid, phosphoric acid, tartaric acid, potassium bitartrate, sodium acetate, sorbitol, and preferably EDTA.

According to one embodiment, the composition comprises a monoglyceride content of 1 to 20%, a content of tartaric ester of monoglyceride 0.05% to 2%, from 0.1% to 4% of pigments and/or mineral fillers coated, and optionally from 0.01% to 1% of sequestering agent, the percentages being expressed by mass relative to the mass of the total composition.

According to one embodiment, the composition comprises a monoglyceride content of 2 to 10%, a monoglyceride tartaric ester content of 0.1 to 1%, %, preferably from 0.1% to 3% of pigments and/or coated mineral fillers, and optionally from 0.01% to 1% of sequestering agent, the percentages being expressed by mass relative to the mass of the total composition.

According to one embodiment, the composition comprises a monoglyceride content of from 3 to 8%, a tartaric ester of monoglyceride content, 0.1 to 0.5% of pigments and/or mineral fillers coated, and optionally of 0.05 to 0.5% sequestering agent, the percentages being expressed by mass relative to the mass of the total composition.

The invention specifically covers a composition comprising as ingredients: MONOGLYCERIDE; ESTERS OF TARTARIC MONOGLYCERIDES; OXIDE COATED TITANIUM POLYDIMETHYLSILOXANE; and possibly: ACID ETHYLENE DIAMINE TETRACETIC, DISODIUM SALT; associated for example with: PHENOXYETHANOL; XANTHAN; 2-ACRYLOYLAMINO-2-METHYLPROPANE-1-SULFONIC ACID (AMPS); POLYDIMETHYLSILOXANE (PDMS); WATER; GLYCERINE; PROPYLENE GLYCOL.

Other Ingredients

A certain amount of oil can be introduced into the compositions according to the invention.

One can use one or more oils commonly used in cosmetics, chosen in particular from a mineral, vegetable, silicone oil.

Preferably the oil or oils are present in a total amount ranging from 0.5 to 35% by mass based on the mass of the total composition.

The cosmetic compositions according to the invention may contain the usual ingredients or additives in cosmetics: pigments, dyes, biological assets (anti-aging agents, anti-oily skin, skin whitening, anti-perspirant, anti-oxidants, etc.) sunscreens, film-forming polymers, scattering fillers, oils and fats, moisturizers, emollients, and any combination thereof.

The invention also relates to the use of at least one coated pigment and/or at least one coated mineral filler, optionally in combination with at least one sequestering agent, for improving the stability of a composition, especially a cosmetic composition comprising at least one monoglyceride and at least one diacetyl tartaric ester of monoglyceride.

The invention also relates to a cosmetic treatment method comprising applying a composition as defined according to the invention on an area of skin, in particular to limit the gloss or shiny appearance of the skin at the area application, especially in a tropical climate.

This invention will now be described more specifically through examples that are in no way imitative of the scope of the invention. However, the examples provide information about specific characteristics, variants and preferred embodiments of the invention.

In the examples, the temperature is given in degrees Celsius and is the ambient temperature (20-25° C.), unless mentioned otherwise, and the pressure is the atmospheric pressure at sea level unless mentioned otherwise. Furthermore, percentages are given in mass relative to the total mass, unless mentioned otherwise.

EXAMPLES

Example 1 and 2: Preparation of Cosmetic Compositions According to this Invention

TABLE 1

| Chemical Name | EXAMPLE 1 | EXAMPLE 2 | PHASES |
|---|---|---|---|
| MONOGLYCERIDE - TEGIN 90 PELLETS EVONIK | 5 | 5 | A |
| ESTER OF TARTARIC MONOGLYCERIDES - PANODAN A2020 KOSHER DANISCO | 0.2* | 0.2* | |
| PHENOXYETHANOL | 0.5 | 0.5 | |
| WATER | 83 | 82.5 | |
| ETHYLENE DIAMINE TETRACETIC ACID, DISODIUM SALT | — | 0.1 | |
| GLYCERIN | 5 | 5 | B |
| PROPYLENE GLYCOL | 2 | 2 | |
| XANTHAN GUM | 0.2 | 0.2 | C |
| ACRYLAMIDE/SODIUM ACRYLOYLDIMETHYLTAURATE COPOLYMER (and) ISOHEXADECANE (and) POLYSORBATE 80 | 2 | 2 | |
| POLY DIMETHYLSILOXANE (5 cst) | 2 | 2 | |
| OXIDE COATED TITANIUM POLYDIMETHYLSILOXANE (98/2) (CI: 77891) | 0.5 | 0.5 | |

*0.2% to 80% by mass of Active Material (AM)

1/ Fill the mixture of phase A in a melter, keep the temperature at 65° C. for 45 minutes with stirring at 250 rpm until a homogeneous and opalescent phase.

2/ Add phase B, stopping the flow of heat and cool with vigorous stirring between 400 and 600 rpm 3/ In the end, add phase C comprising the polymer and the charge stirred at room temperature.

Example 3: Stability of Compositions According to the Invention

TABLE 2

| Chemical name | COMPARATIVE | EXAMPLE 3 | EXAMPLE 4 |
|---|---|---|---|
| ETHYLENE DIAMINE TETRACETIC ACID, DISODIUM SALT | — | — | 0.1 |
| OXIDE COATED TITANIUM POLYDIMETHYLSILOXANE | — | 0.5 | 0.5 |
| PHENOXYETHANOL | 0.5 | 0.5 | 0.5 |
| XANTHAN GUM | 0.2 | 0.2 | 0.2 |
| ACRYLAMIDE/SODIUM ACRYLOYLDIMETHYLTAURATE COPOLYMER (and) ISOHEXADECANE (and) POLYSORBATE 80 - SIMULGEL 600 - SEPPIC | 2 | 2 | 2 |
| PDMS | 2 | 2 | 2 |
| WATER | 83.1 | 83 | 82.5 |
| GLYCERIN | 5 | 5 | 5 |
| PROPYLENE GLYCOL | 2 | 2 | 2 |
| MONOGLYCERIDE - TEGIN 90 PELLETS EVONIK | 5 | 5 | 5 |
| ESTER OF TARTARIC MONOGLYCERIDES - PANODAN A2020 KOSHER DANISCO | 0.2* | 0.2* | 0.2* |

*0.2% to 80% by mass of Active Material (AM)

To evaluate the storage stability of compositions according to the invention subjected to an accelerated aging test that is to store a week in an oven thermostated at 55° C.

TABLE 3

| | COMPARATIVE | EXAMPLE 1 | EXAMPLE 2 |
|---|---|---|---|
| Change in the macroscopic aspect after 1 week at 55° C. | Unstable: becomes pearlescent and opalescent | Compliant (identical to cool type) Stable: smooth white cream | Compliant (identical to cool type) Stable: smooth white cream |

"Cool type" means the formulation of the example under consideration after preparation of the formulation but before implementation of the accelerated aging test.

The compositions of the invention are stable in a satisfactory manner, and are therefore compliant with the objective sought.

Perceived Performance

A formula of the invention has been tested by women with oily skin in India, China and Brazil (self-application on 14 women for 7 days). At the end of the trial period, the women are satisfied with the performance and cosmetic decomposition properties of the invention. The effectiveness of the compositions of the invention in the fight against sheen or gloss of the skin during the day is perceived in the three countries. The product meets the expectations of individuals with oily skin, in particular in a tropical climate.

Women who applied on their skin the compositions of the present invention consider that they are comfortable, that is to say, the application does not present any particular discomfort but instead provides a feeling of comfort and effect of skin hydration.

The compositions of the invention therefore meet the challenges set out initially.

A non-compliant form of the invention has been tested and does not achieve a satisfactory result in terms of matteness.

The invention claimed is:

1. A cosmetic treatment method for limiting the gloss or shiny appearance of the skin and/or providing a skin hydration effect, said method comprising applying a composition on an area of skin of a subject in need of limiting the gloss or shiny appearance of the skin and/or providing a skin hydration effect, said composition comprising an aqueous phase and at least one coated pigment and/or at least coated mineral filler, said composition further comprising a lipogel phase comprising (i) at least one monoglyceride and (ii) at least one tartaric ester of monoglyceride, wherein the at least one monoglyceride comprises a saturated or unsaturated alkyl chain of 12 to 22 carbon atoms and wherein the monoglyceride content is from 1% to 20% by mass based on the total mass of said composition and wherein the tartaric ester of monoglyceride content is from 0.1% to 1% by mass based on the total mass of said composition, wherein said composition limits the gloss or shiny appearance of the skin and/or provides a skin hydration effect at the area of application of said composition.

2. The cosmetic treatment method, according to claim 1, wherein said method is for limiting the gloss or shiny appearance of the skin in a tropical climate at the area of application of said composition.

3. The cosmetic treatment method, according to claim 1, wherein the composition comprises more than 50% in mass of aqueous phase relative to the total mass of the composition.

4. The cosmetic treatment method, according to claim 1, wherein the monoglyceride comprises a saturated or unsaturated alkyl chain of 16 or 18 carbon atoms.

5. The cosmetic treatment method, according to claim 1, wherein the tartaric ester of monoglyceride is a diacetyl tartaric ester of monoglyceride comprising a saturated or unsaturated alkyl chain of 12 to 22 carbon atoms.

6. The cosmetic treatment method, according to claim 1, wherein the at least one coated pigment and/or the at least coated mineral filler is coated with at least one hydrophobic or lipophilic-treating agent selected from silicone surfactants; fluorinated surfactants; fluorosilicone surfactants; metal soaps amino N-acylamino acids or salts thereof; lecithin and its derivatives; triisostearyl isopropyl titanate; isostearyl sebacate; plant or animal natural waxes, synthetic waxes polar; fatty esters; fatty alcohols; phospholipids; and mixtures thereof.

7. The cosmetic treatment method, according to claim 1, wherein the coated content of the at least one coated pigment and/or the at least coated mineral filler is from 0.1% to 4% by mass based on the total mass of said composition.

8. The cosmetic treatment method according to claim 6, wherein the hydrophobic or lipophilic-treating agent represent from 0.1 to 50% by mass of the total mass of the coated pigment and the coated mineral filler.

9. The cosmetic treatment method, according to claim 1, wherein the composition comprises a least one sequestering agent.

10. The cosmetic treatment method according to claim 1, wherein the composition comprises a least one sequestering agent selected from ethylene diamine tetraacetic acid (EDTA), glucono delta-lactone, sodium gluconate, potassium and/or calcium; citric acid, phosphoric acid, tartaric acid, potassium bitartrate, sodium acetate, sorbitol and any combination thereof.

11. The cosmetic treatment method, according to claim 1, wherein the composition comprises a sequestering agent from 0.01% to 1% by mass based on the total mass of said composition.

* * * * *